US007543584B2

(12) United States Patent
Brookman

(10) Patent No.: US 7,543,584 B2
(45) Date of Patent: Jun. 9, 2009

(54) POWERED AIR PURIFYING RESPIRATOR SYSTEM AND BREATHING APPARATUS

(75) Inventor: Michael J. Brookman, Branford, CT (US)

(73) Assignee: Interspiro, Inc., Pleasant Prairie, WI (US)

( * ) Notice: Subject to any disclaimer, the term of this patent is extended or adjusted under 35 U.S.C. 154(b) by 0 days.

(21) Appl. No.: 10/675,135

(22) Filed: Sep. 29, 2003

(65) Prior Publication Data

US 2004/0182395 A1 Sep. 23, 2004

Related U.S. Application Data

(63) Continuation of application No. 10/393,346, filed on Mar. 21, 2003.

(51) Int. Cl.
*A61M 16/00* (2006.01)
*A62B 7/00* (2006.01)
*A62B 9/00* (2006.01)

(52) U.S. Cl. ............................ 128/205.11; 128/205.22; 128/204.18; 128/204.26

(58) Field of Classification Search ............ 128/201.25, 128/204.26, 205.22, 201.28, 204.23, 204.21, 128/205.21, 202.26, 205.28, 204.29, 204.18, 128/205.29, 205.27, 200.24
See application file for complete search history.

(56) References Cited

U.S. PATENT DOCUMENTS

| | | | | |
|---|---|---|---|---|
| 2,085,249 | A | 6/1937 | Bullard | |
| 2,284,054 | A * | 5/1942 | Siegwart | 128/204.25 |
| 2,332,662 | A | 10/1943 | Nathanson | |
| 2,999,497 | A | 9/1961 | Hamilton et al. | |
| 3,000,805 | A | 9/1961 | Carritt et al. | |
| 3,202,150 | A | 8/1965 | Miller | |
| 3,456,642 | A * | 7/1969 | Cupp | 128/204.26 |
| 3,508,542 | A * | 4/1970 | Browner | 128/202.22 |
| 3,556,098 | A | 1/1971 | Kanwisher | |
| 3,657,740 | A | 4/1972 | Cialone | |
| 3,739,774 | A | 6/1973 | Gregory | |
| 4,019,507 | A | 4/1977 | Oetjen et al. | |
| 4,146,887 | A * | 3/1979 | Magnante | 340/632 |
| 4,233,972 | A | 11/1980 | Hauff et al. | |
| 4,273,120 | A * | 6/1981 | Oswell | 128/204.26 |

(Continued)

FOREIGN PATENT DOCUMENTS

| | | |
|---|---|---|
| DE | 35 12 644 | 10/1986 |

(Continued)

OTHER PUBLICATIONS

International Search Report issued in PCT/US2004/0054668 completed on Aug. 4, 2004.

(Continued)

*Primary Examiner*—Justine R Yu
*Assistant Examiner*—Annette F Dixon
(74) *Attorney, Agent, or Firm*—Marshall, Gerstein & Borun LLP

(57) ABSTRACT

A combination of an SCBA system for providing bottled air to a user and a PAPR system for purifying ambient air for use by a user wherein the two systems are used alternatingly depending on the contaminated condition of the ambient air and the oxygen content of the ambient air.

28 Claims, 7 Drawing Sheets

U.S. PATENT DOCUMENTS

| | | | | | |
|---|---|---|---|---|---|
| 4,417,575 | A | | 11/1983 | Hilton et al. | |
| 4,419,994 | A | | 12/1983 | Hilton | |
| 4,423,723 | A | | 1/1984 | Winkler et al. | |
| 4,430,995 | A | * | 2/1984 | Hilton | 128/204.21 |
| 4,433,685 | A | * | 2/1984 | Giorgini et al. | 128/204.26 |
| 4,440,162 | A | | 4/1984 | Sewell et al. | |
| 4,440,163 | A | * | 4/1984 | Spergel | 128/205.13 |
| 4,449,524 | A | * | 5/1984 | Gray | 128/202.27 |
| 4,462,399 | A | | 7/1984 | Braun | |
| 4,463,755 | A | | 8/1984 | Suzuki | |
| 4,510,193 | A | | 4/1985 | Blucher et al. | |
| 4,567,889 | A | | 2/1986 | Lehmann | |
| 4,572,323 | A | | 2/1986 | Randall | |
| 4,590,951 | A | * | 5/1986 | O'Connor | 128/204.23 |
| 4,612,239 | A | | 9/1986 | Dimanshteyn | |
| 4,633,868 | A | * | 1/1987 | Itoh et al. | 128/204.26 |
| 4,674,479 | A | | 6/1987 | Jennings et al. | |
| D295,046 | S | | 4/1988 | Odell | |
| 4,741,332 | A | * | 5/1988 | Beaussant | 128/201.33 |
| 4,765,326 | A | | 8/1988 | Pieper | |
| 4,841,953 | A | | 6/1989 | Dodrill | |
| 4,873,970 | A | * | 10/1989 | Freidank et al. | 128/202.22 |
| 4,886,056 | A | * | 12/1989 | Simpson | 128/201.25 |
| 4,887,638 | A | | 12/1989 | Hellquist et al. | |
| 4,899,740 | A | | 2/1990 | Napolitano | |
| 4,905,683 | A | | 3/1990 | Cronjaeger | |
| 4,926,855 | A | | 5/1990 | Hellquist et al. | |
| 4,961,763 | A | * | 10/1990 | Thompson et al. | 55/312 |
| 4,971,052 | A | | 11/1990 | Edwards | |
| 5,018,518 | A | * | 5/1991 | Hubner | 128/202.22 |
| 5,035,239 | A | | 7/1991 | Edwards | |
| 5,078,130 | A | * | 1/1992 | Van Oosten et al. | 128/201.24 |
| 5,080,414 | A | | 1/1992 | Hellquist et al. | |
| 5,097,826 | A | | 3/1992 | Gray et al. | |
| 5,112,666 | A | | 5/1992 | Langston | |
| 5,125,402 | A | | 6/1992 | Greenough et al. | |
| 5,127,896 | A | | 7/1992 | de Gaston | |
| 5,161,525 | A | * | 11/1992 | Kimm et al. | 128/204.26 |
| 5,221,572 | A | | 6/1993 | Meunier | |
| 5,265,592 | A | | 11/1993 | Beaussant | |
| 5,370,112 | A | * | 12/1994 | Perkins | 128/204.21 |
| 5,390,666 | A | * | 2/1995 | Kimm et al. | 128/204.26 |
| 5,461,934 | A | * | 10/1995 | Budd | 73/864.52 |
| 5,477,850 | A | | 12/1995 | Zegler et al. | |
| 5,584,286 | A | | 12/1996 | Kippax | |
| 5,611,485 | A | * | 3/1997 | Davis | 239/8 |
| 5,626,947 | A | | 5/1997 | Hauer et al. | |
| 5,660,171 | A | * | 8/1997 | Kimm et al. | 128/204.23 |
| 5,743,775 | A | | 4/1998 | Baurmeister | |
| 5,832,916 | A | | 11/1998 | Lundberg | |
| 5,950,621 | A | * | 9/1999 | Klockseth et al. | 128/204.26 |
| 6,102,034 | A | | 8/2000 | Buhlmann | |
| 6,105,632 | A | | 8/2000 | Buhlmann | |
| 6,167,882 | B1 | | 1/2001 | Almqvist et al. | |
| 6,269,811 | B1 | * | 8/2001 | Duff et al. | 128/204.21 |
| 6,290,111 | B1 | | 9/2001 | Hedenberg et al. | |
| 6,328,031 | B1 | | 12/2001 | Tischer et al. | |
| 6,344,071 | B1 | * | 2/2002 | Smith et al. | 95/274 |
| 6,360,741 | B2 | * | 3/2002 | Truschel | 128/202.22 |
| 6,360,742 | B1 | | 3/2002 | Maxwell et al. | |
| 6,626,175 | B2 | * | 9/2003 | Jafari et al. | 128/204.21 |
| 6,655,383 | B1 | * | 12/2003 | Lundberg | 128/205.23 |
| 6,758,213 | B1 | | 7/2004 | Brekken et al. | |
| 7,077,133 | B2 | * | 7/2006 | Yagi et al. | 128/204.26 |
| 7,086,397 | B2 | * | 8/2006 | Spruiell | 128/200.24 |

FOREIGN PATENT DOCUMENTS

| | | | | |
|---|---|---|---|---|
| DE | 195 03 027 | | | 3/1996 |
| DE | 19503027 | | * | 3/1996 |
| EP | 0 094 757 | | | 11/1983 |
| EP | 241 188 | A1 | | 10/1987 |
| FR | 8144750 | | | 6/1937 |
| FR | 886 782 | | | 10/1943 |
| FR | 2 514 934 | | | 10/1981 |
| GB | 2025316 | | | 1/1980 |
| GB | 1 587 812 | | | 4/1981 |
| WO | WO 00/57738 | | | 10/2000 |
| WO | WO 01/32266 | A | | 5/2001 |
| WO | WO-01/41873 | | | 6/2001 |
| WO | WO-03/086541 | | | 10/2003 |

OTHER PUBLICATIONS

Written Opinion issued in PCT/US2004/005668 application mailed Aug. 11, 2004.

A Fax purportedly sent to the U.S.Naval Inventory Control Point, Dave Duval, from Wilcox Industries Corp., Robert F. Guarasi, dated Aug. 23, 2002, 9 pages.

A SCOUT System (Self Contained Operational Utility Tank) brochure, Order No. 20000G01, Wilcox Industries Corp., 2002, 2 pages.

A Wilcox Industries Corp. Invoice No. 2328-0104-00, dated Dec. 31, 2002, 2 pages.

A Milestone Schedule, SCOUT Production, dated Thursday, Aug. 15, 2002, 1 page.

Partial International Search Report mailed on Dec. 12, 2005 for PCT/US2005/025976, 2 pages.

International Search Report mailed Apr. 13, 2006 for PCT/US2004/025976, 2 pages.

Written Opinion of the International Searching Authority mailed Apr. 13, 2006 for PCT/US2004/025976, 9 pages.

European Search Report for Application No. 08017362.8, dated Mar. 18, 2009.

* cited by examiner

POWERED AIR PURIFYING RESPIRATOR SYSTEM AND BREATHING APPARATUS

RELATED APPLICATIONS

This application is a continuation of U.S. patent application Ser. No. 10/393,346, filed Mar. 21, 2003, entitled "Powered Air Purifying Respirator System and Breathing Apparatus."

FIELD OF TECHNOLOGY

This invention is directed to an apparatus for assisting persons to breath in hostile environments. It more particularly relates to such an apparatus that is useful in purifying contaminated air as well as providing portable clean air.

BACKGROUND

There are, at present two systems for assisting the breathing of persons who are subject to contaminated air. First, there are the powered respirators (SCBA-Self Contained Breathing Apparatus) that feed compressed (e.g. bottled) air to a tight fitting face mask, or other conduit to the mouth and/or nose, for inhaling by the user. These systems do not permit the user access to the ambient atmosphere at all. Second, there are filter/decontamination systems for use in the form of a canister, in connection with a respirator apparatus that rely on cleaning ambient atmosphere to make it suitable for breathing. Such filter systems may or may not make use of auxiliary power. In powered systems, ambient atmosphere is sucked through a suitable filter/decontamination means, or other purifying means, by a powered fan or the like, such that the contaminated ambient air is rendered breathable. The purified resultant air is fed to a headpiece of some kind, such as a tight fitting facemask (the complete system is known as a Powered Air Purifying Respirator (PAPR)). Both types of breathing assists are used by personnel who are subject to breathing ambient atmosphere that would otherwise be considered to be harmfully contaminated, unbreathable or dangerous air.

A dangerous or unbreathable atmosphere is considered to be air containing less than 19.5 volume percent oxygen, or air with the requisite oxygen, but also containing significant proportions of harmful contaminants, e.g. particulate or gaseous, is considered contaminated and harmful. It will be appreciated that, in some situations, (where the oxygen content is at least 19.5%), the wearer maybe able to enter an area that has a contaminated atmosphere using only a filter system provided the filter(s) is capable of meeting the challenge of the contamination whereby cleaning the atmosphere and enabling the user to breath and still preserve his health. The filter can be provided with means to eliminate harmful constituents in the wearer's ambient atmosphere. In particular, filter based decontamination systems, that is those systems that purify an ambient atmosphere that has become contaminated so as to convert it to breathable air, work best when they pass an air supply under positive pressure through a cleaning element (such as a suitable filter). That is, a pump/fan is used to suck the contaminated atmosphere through a filter, and perhaps into contact with a material that ameliorates the contaminant(s), and to then force the purified, e.g. filtered, air under positive pressure into a face mask or other means associated with the breathing of the wearer, such as a mouth grip, hood or helmet. While a powered air supplying means, such as a battery operated pump/fan means, is probably preferred, it is also known that air cleaning systems that are not powered by external means can be used. In these unpowered systems, the user's lung power provides the necessary impetus to force contaminated air through the cleaning element and feed it to the user. For simplicity, this means of cleaning ambient atmosphere will be referred to as an Air Purifying Respirator (APR). When the air is forced through the system due to the use of a battery, line current or other powered pump or fan arrangement, these operating systems are known as a Powered Air Purifying Respirator (PAPR)

A powered air purifying respirator system (PAPR) will protect against contaminants so long as the oxygen level in the purified air is above 19.5 volume percent and provided the contaminants are such as can be removed by filtration, e.g. soot and smoke, and/or can be ameliorated by reaction with a suitable purifying material. In practical effect, these systems have been designed to use replaceable filter(s) and air purifying canister(s). However, they are of no value where the ambient atmosphere has an oxygen content that is less than 19.5% by volume.

Other situations exist, such as where the ambient atmosphere is so contaminated, or the contamination is such, that a filter and/or decontamination/purifier system cannot handle the problem; and/or the oxygen content of the ambient air is too low to satisfy human survival needs (that is, where the atmosphere is IDLH, that means the ambient atmosphere is of Immediate Danger to Life and Health). In those circumstances, a person entering the area with such level and type of contamination must take his own air supply along with him. This is akin to a SCUBA diver carrying his air with him in the form of a container (bottle) with compressed, clean air in it. One problem is that a wearer of a SCBA must support all of the weight of the bottled air whereas, in water, a diver has the advantage of the water's buoyancy to help support the weight of the SCUBA tanks. Even so, most SCBA systems are only capable of carrying enough bottled, compressed air for up to about an hour's use. It would, of course, be most desirable to be able to increase the time that a user, for example a fire fighter, can work in a hostile environment dependent upon bottled air while at the same time minimizing the weight that the person must carry to support him for that additional time.

It will be appreciated that air bottles are heavy, especially when they are full. In the case of fire fighters, they are already going into an unfriendly environment carrying their tools with them, and the heat of the fire makes it even more difficult to carry the extra weight of the compressed air container. Further, the fire fighter must often proceed, from the safe ambient air outside the area where a fire has merely contaminated the atmosphere to an extent such that it can be cleaned, by wearing some form of APR, for a relatively long distance before he reaches an area where the contamination is of such an extent that the atmosphere cannot be reasonably cleaned and where he must breath the air he brought with him, or strangle from lack of oxygen, or be harmed by other contaminants.

When carrying around ones' own air supply, there is a very real practical limit as to how much air can be safely carried. Contrary to operating under water with a SCUBA rig, the air bottles used by fire fighters are quite heavy, must be supported entirely by the wearer, and do not have the advantage of water buoyancy partially supporting their weight. Making them larger, to be able to carry more air, increases their weight but decreases their portability. This combination of weight and working conditions severely limits the time that a fire fighter, who is wearing/carrying his own air supply and tools, can effectively fight the fire.

Thus, there exists a situation in which a fire fighter, for example, does not need carried air for some portion of the time that he is working on the fire, but does need portable, bottled air for other portions of the time that he is working on the fire. Yet, existing systems are suited to one or the other; that is, the existing systems either provide positive pressure (pumped) filtering and purification systems to convert contaminated ambient atmosphere to air that is clean enough to breath safely, or they provide bottled air under pressure that is carried by the person to be used instead of the ambient atmosphere. While both systems have deficiencies, each system has advantages, even necessities, under critical conditions.

The above and following comments use a fire fighter as illustrative of the type of person who will benefit from using the instant invention. However, this invention is by no means limited in use to fire fighters. Workers in chemical plants and refineries will have substantial need for the benefits available from the instant invented system. Soldiers in the field that are being subjected to chemical or biological attack will benefit greatly from the instant system. It will be apparent to those of ordinary skill in this art that others will similarly be assisted by the instant invention.

SUMMARY OF DISCLOSURE

One aspect of this invention is a breathing assisting apparatus comprising a tight fitting face mask, or other conventional means of bringing respirating air to a person in need thereof, that is adapted to be tightly fitted to a person's face or mouth or nose (or any combination thereof). For ease of understanding, further reference will be made to the use of a face mask. However, this use is illustrative and not limiting. A mouth piece can also serve the function of bringing the breathable air to the user.

Under complete manual operation, the PAPR and SCBA are each connected to the face mask by its own breathing hose, each with its own entry point, in the case of a dual entry face mask, or, via a "tee" piece, or similar connection device in the case of a single entry face mask. At or about the face mask each is provided with a non-return (one way) valve. An exhaust valve is provided in the face mask so that exhaust air is vented to the atmosphere. A valving and/or switching system is provided so that the wearer controls whether to receive cleaned ambient air or supplied (bottled) air. This valving and/or switching system can be manually operated by the user, in which case the user determines independently, which air supply to use; or it can operate under semi-automatic control where the air supply from the SCBA and the PAPR are both connected to a valve manifold. On start up, the SCBA supply is in a shut off condition and the PAPR is in an on condition. Air is passed to the face mask via the PAPR. Either at the discretion of the wearer or in response to an audible and/or visual alarm which operates based on sampling and testing the ambient air and indicates by way of the alarm that the system should be switched from PAPR to SCBA operation, the wearer opens the SCBA supply valve and then switches off the PAPR. The pressure of the SCBA air, on exhaust, will shuttle a manifold valve automatically switching off the PAPR leaving the air supply solely on SCBA. In the alternative, the decision as to whether to accept purified air from the canister/filter assembly, or to demand air from the supplied air bottle means; can operate automatically based on sampling and testing means associated with the valving means which would be electrically operated so as to open access to the SCBA and close access to the PAPR via the manifold valve.

At least one air bottle is provided with a connection to at least one port in the face mask and a controllable valve is provided that permits control as to whether to withdraw air from the bottle(s) or not. At least one filter or canister is provided, separate from the air bottle(s), also with a controllable valve system that permits control as to whether ambient air is taken in by the PAPR and fed to the mask. A battery or other powered electric motor driven fan, that is operatively attached between the filter or canister and to the user, is provided with means, such as a switch or a handle, to enable the motor driven fan to be operated or not.

Thus, when the ambient air has sufficient oxygen content, and the contaminants are suited to removal by filtration or chemical treatment in the canister, the fan can be activated by operating the switch and ambient air will be powered through the filter or canister where it is purified of its harmful constituents, such as soot and other harmful particles, vapors or gases. Under manual operation when the ambient air has insufficient oxygen, or the contaminants are such that they cannot be removed by filtration or other treatment in the filter(s) or canister(s), the valve of the SCBA is opened by the wearer, and the PAPR is switched off. Ambient air is no longer taken in through the filter(s)/canister(s). Instead, it is now being supplied by the SCBA.

Where a face mask is used, it is suitably equipped with a one way valve that enables exhausted, exhaled air to be vented regardless whether the intake air was derived through the filter canister or from the bottled compressed air. It is considered to be within the scope of this invention for it to be used in conjunction with a closed circuit apparatus.

As is conventional, the bottled air, that is under substantial pressure, must have its pressure reduced to an extent sufficient to enable it to be breathed by the user without damage to their respiratory system. This procedure, and equipment to enable this to be accomplished, is well known per se. Suitably, commercially available first and second stage regulators can be used for this purpose. Thus, there are in effect two successive valving systems disposed between the air bottle and the face mask: a first valve that is a simple open or close valve that is attached at or very near the air bottle; and a regulator, pressure reducing valving system that is disposed in the line between the first valve and the face mask.

DETAILED DESCRIPTION

Figure 1:
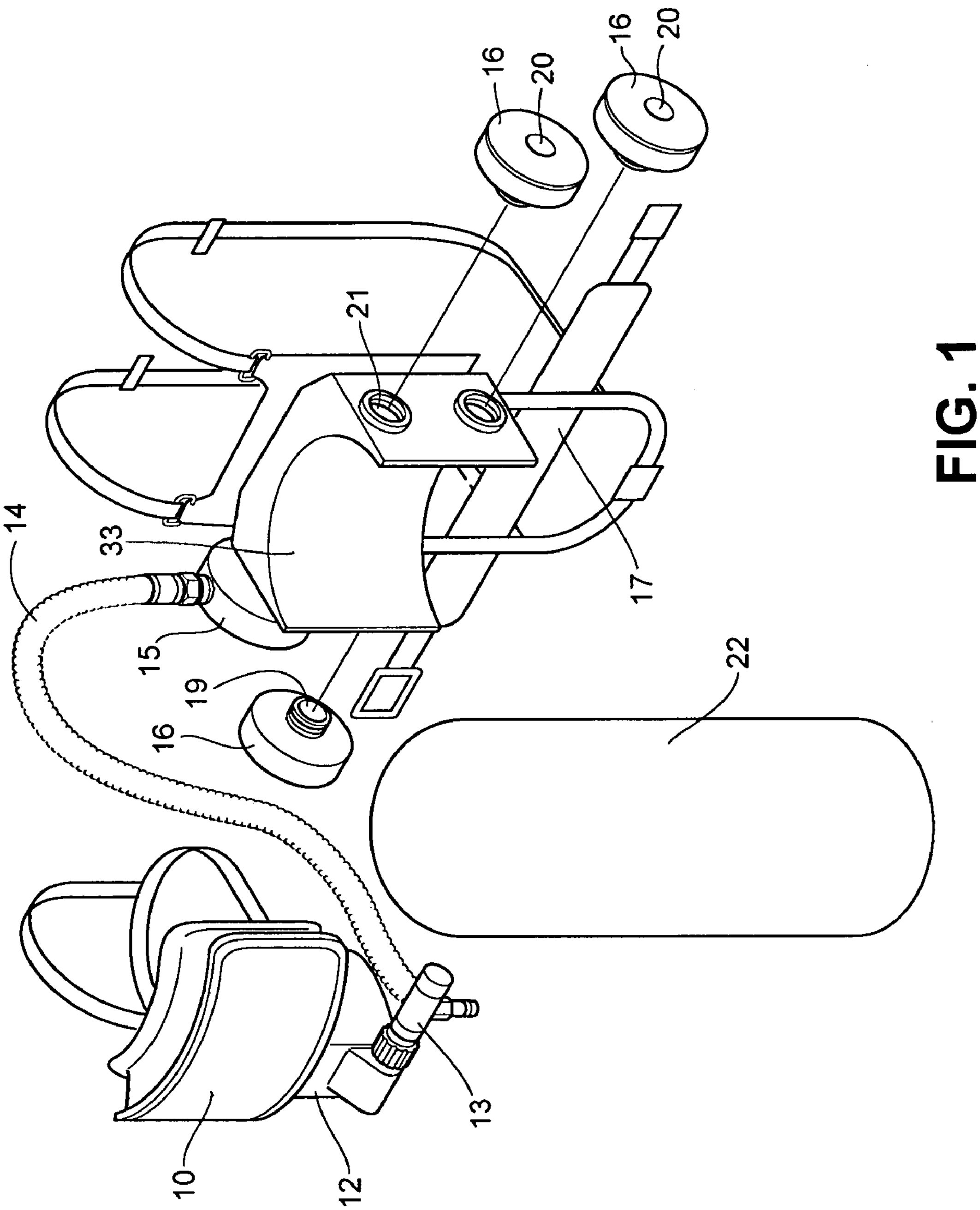
FIG. 1 is an exploded perspective view of an apparatus according to this invention with parts omitted for ease of understanding.
Figure 2:
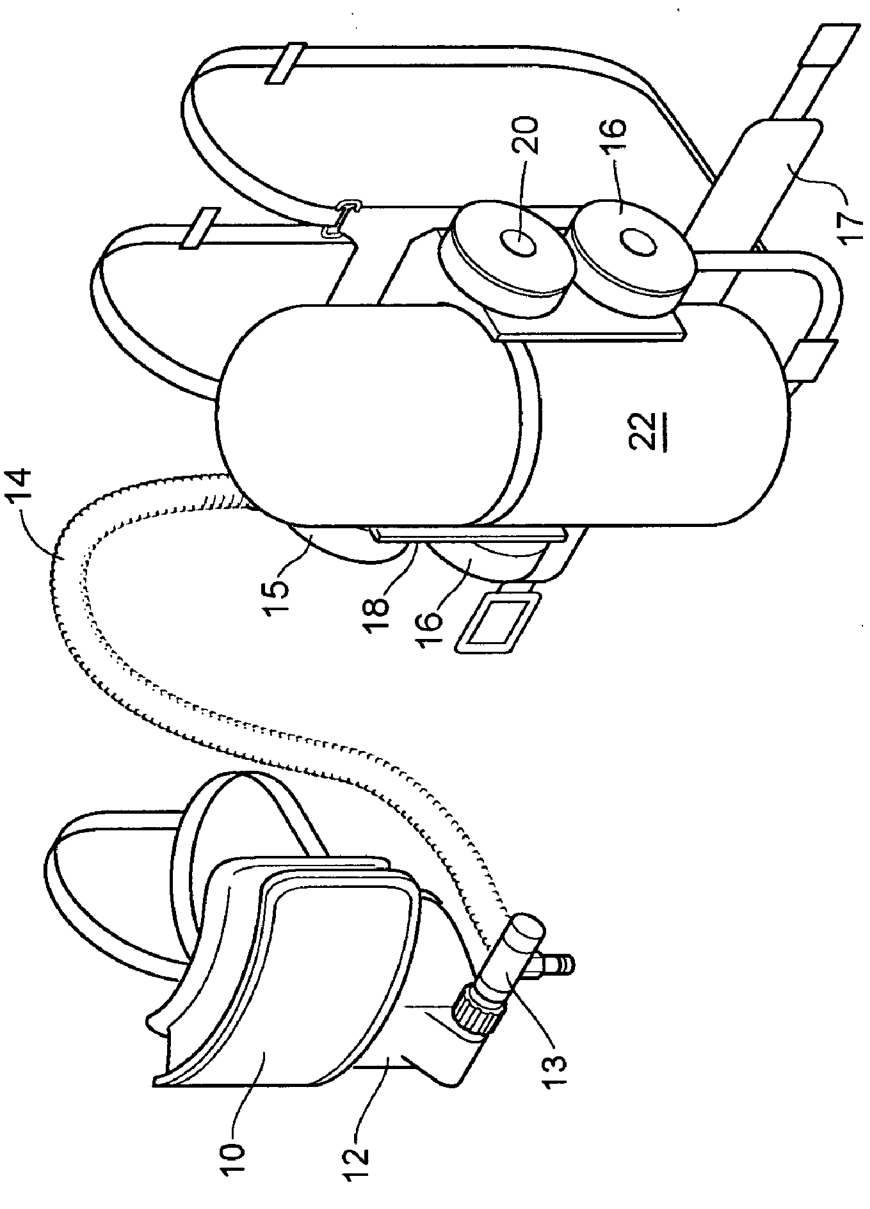
FIG. 2 is a perspective view of one aspect of the apparatus according to this invention in a fully assembled condition; where the PAPR and the SCBA both use a common hose to connect to the face mask.

Referring now to the drawing, there is shown in FIGS. 1 and 2 an apparatus that comprises a face mask 10 that is adapted to be tightly fitted to the face of the wearer against incursion by the ambient atmosphere (for clarity, the user is not shown wearing the mask. Further for clarity, the alternative mouth and/or nose breathing elements are not shown). A hose 14 connects the face mask 10 directly to source of breathable air, such as air that has been cleaned and is forced into the face mask by means of a blower motor and fan assembly 15 (see FIGS. 1, 2 and 6). In this embodiment, the face mask 10 is also connected directly to a compressed air bottle 22 via a hose 27. Note that in this embodiment, the face mask itself is the plenum chamber into which bottled air as well as cleaned ambient air are both forced.

The blower motor and fan assembly 15, is operatively connected to a plenum chamber assembly 18 has attached to it a plurality of filter elements 16. Engaging the impeller fan 25 is adapted to cause ambient air to be drawn through the filter elements 16 which may include filters or canisters containing suitable decontamination elements where the ambient air is to be cleaned of solid particulate matter, harmful gases and/or odors to produce cleaned air. Subject to the class of canisters fitted and the time spent in the contaminated area, the canisters may provide breathable air in a chemically, biologically or nuclear contaminated environment.

The cleaned air, which presumably has sufficient oxygen content, which is adapted to be drawn by the fan 25 into operative relationship with the face mask 10 and thereby provide breathable air to the wearer. The cleaned air can be fed directly to the mask 10, as shown in FIG. 6, or it can be deployed to the face mask 10 through a second plenum chamber 21 as shown in FIGS. 3, 4 and 5.

Thus, one embodiment of this invention separates the source of cleaned ambient air from the source of bottled air (suitably supplied from a normal atmosphere) by providing separate access 30 and 32 to the face mask 10. Each of these separate entry points is suitably adapted to be closed by a valve 34 and 36 which are one way or no return valves. That is, these valves 30 and 32 and the air pressure from the source of air supply for the time being, permit air to flow into the face mask 10 but do not permit the air contents of the face mask to flow out of the face mask back into the alternative source of air supply and purification system. There is also provided a separate valve 38, that is also a one way valve that allows the contents of the face mask 10 to vent from the face mask 10 to ambient atmosphere. This venting valve 38 is so designed that it only opens when the gaseous contents of the facemask 10 are at a pressure greater than ambient.

In other embodiments of this invention, the face mask 10 is connected to a plenum chamber 21 via a hose 14*a*. The plenum chamber 21 is adapted to be fed from the air bottle 22 through a hose 27 via a regulator 12 and a shut off valve 24. The plenum chamber 21 is also adapted to be fed purified air from the filters/decontamination canisters 16 through the fan 25 via hose 29. The plenum chamber 21 can be fed with bottled air or purified air in the alternative.

Figure 3:
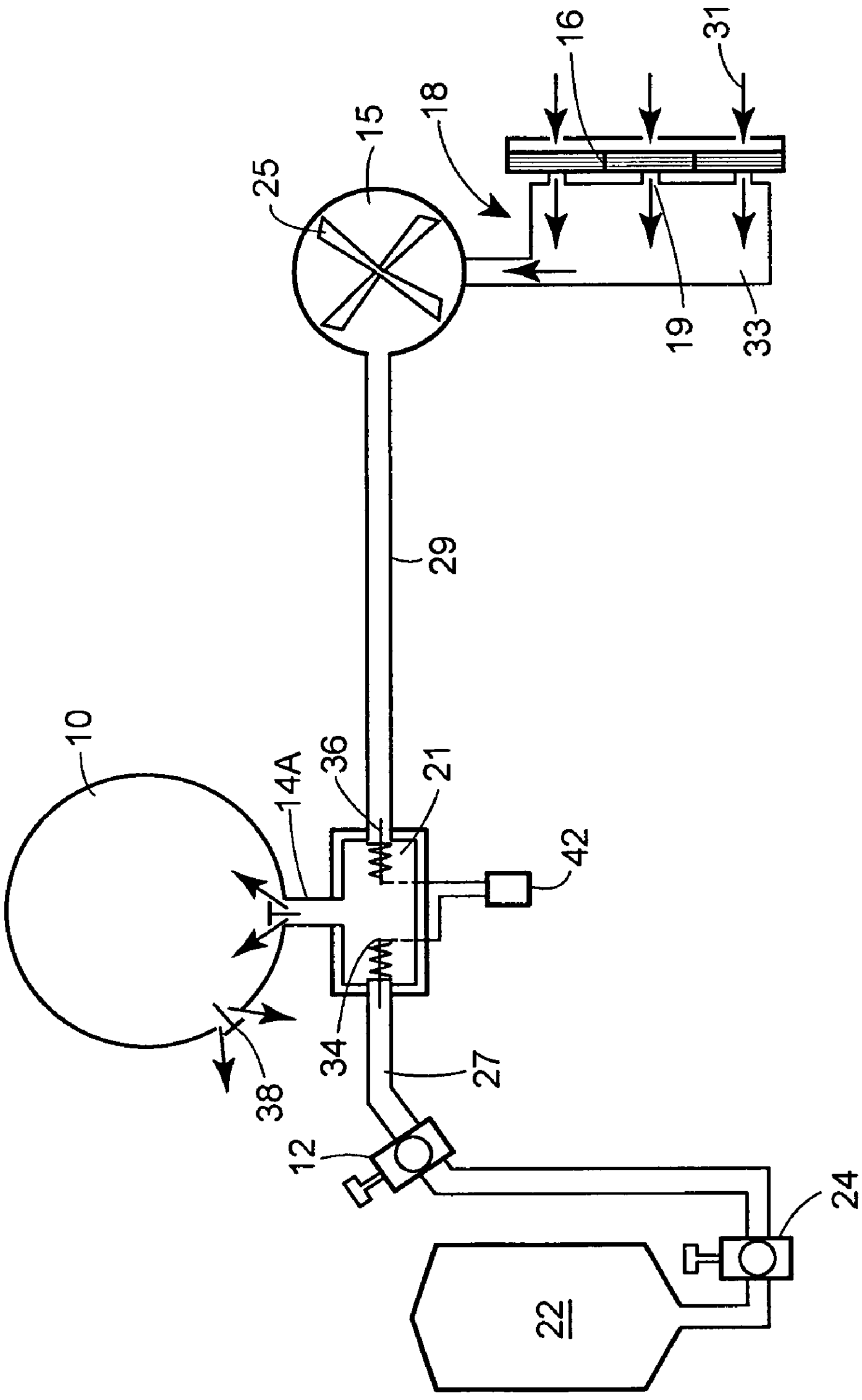
FIG. 3 is a schematic diagram of a first embodiment of an air supply system according to this invention.
Figure 4:
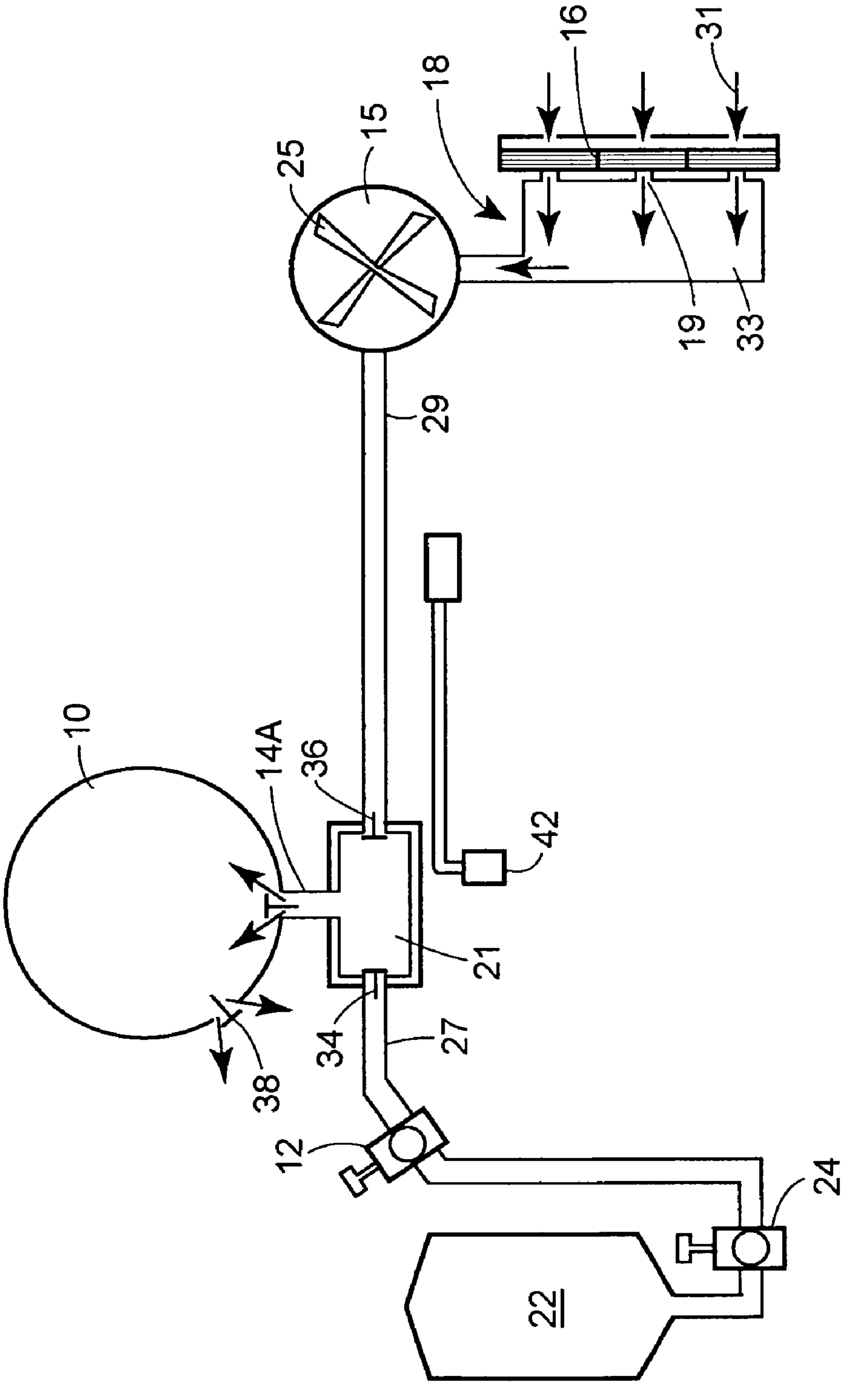
FIG. 4 is a schematic diagram of a second embodiment of an air supply system according to this invention.
Figure 5:
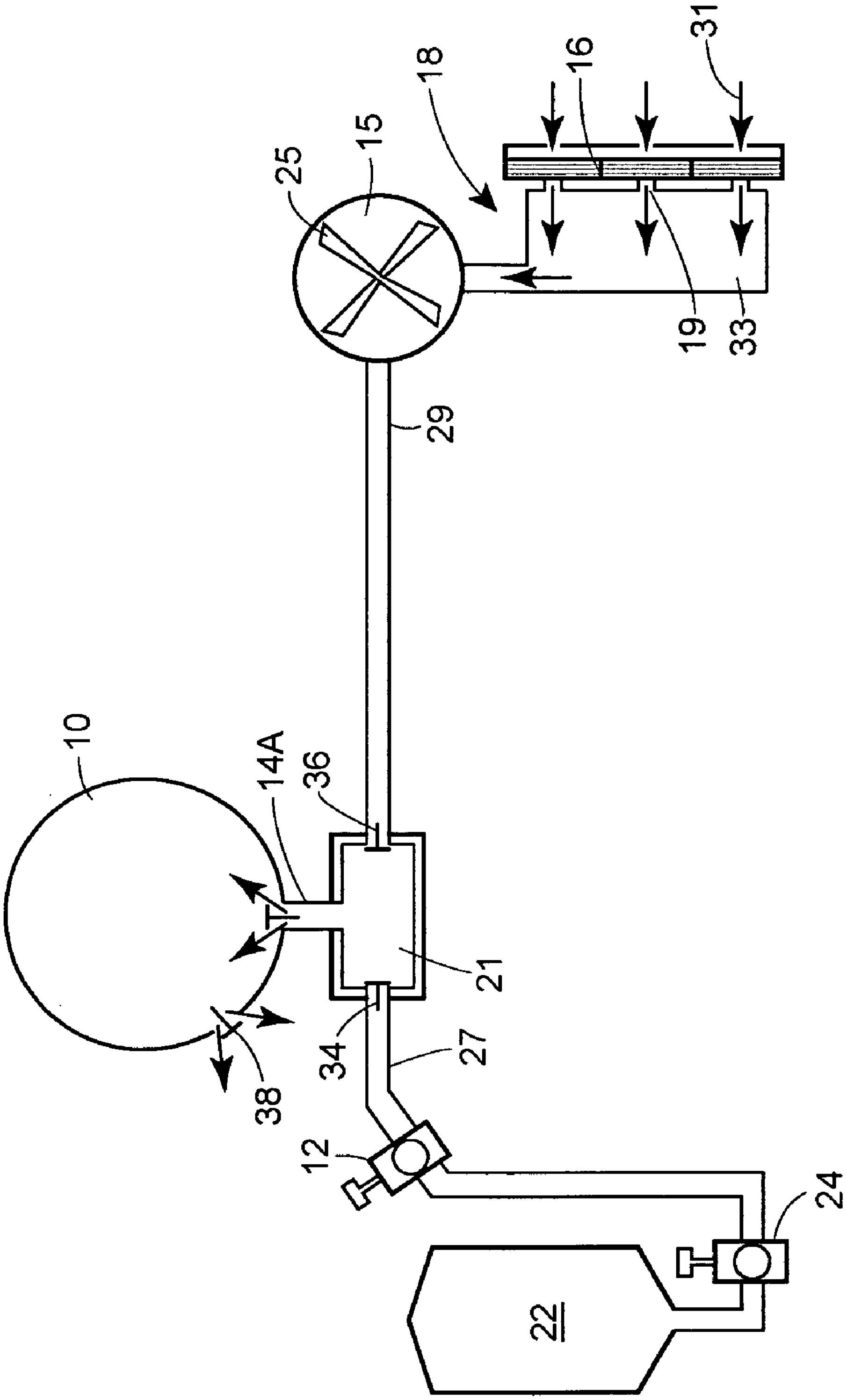
FIG. 5 is a schematic diagram of a third embodiment of an air supply system according to this invention.
Figure 6:
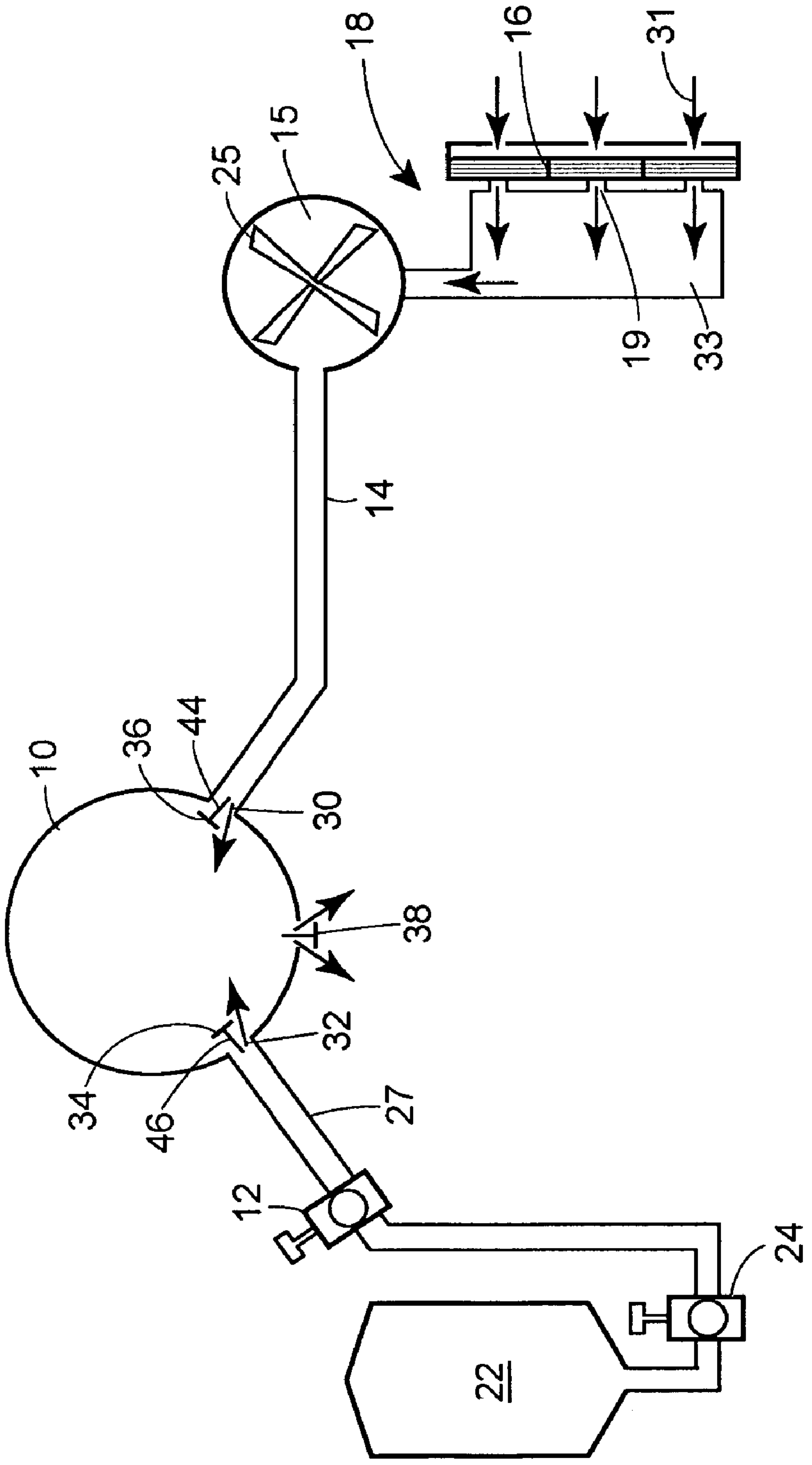
FIG. 6 is a schematic diagram of a fourth embodiment of an air supply system according to this invention and FIG. 7 is a schematic diagram of the fourth embodiment of the invention with some modifications.
Figure 7:
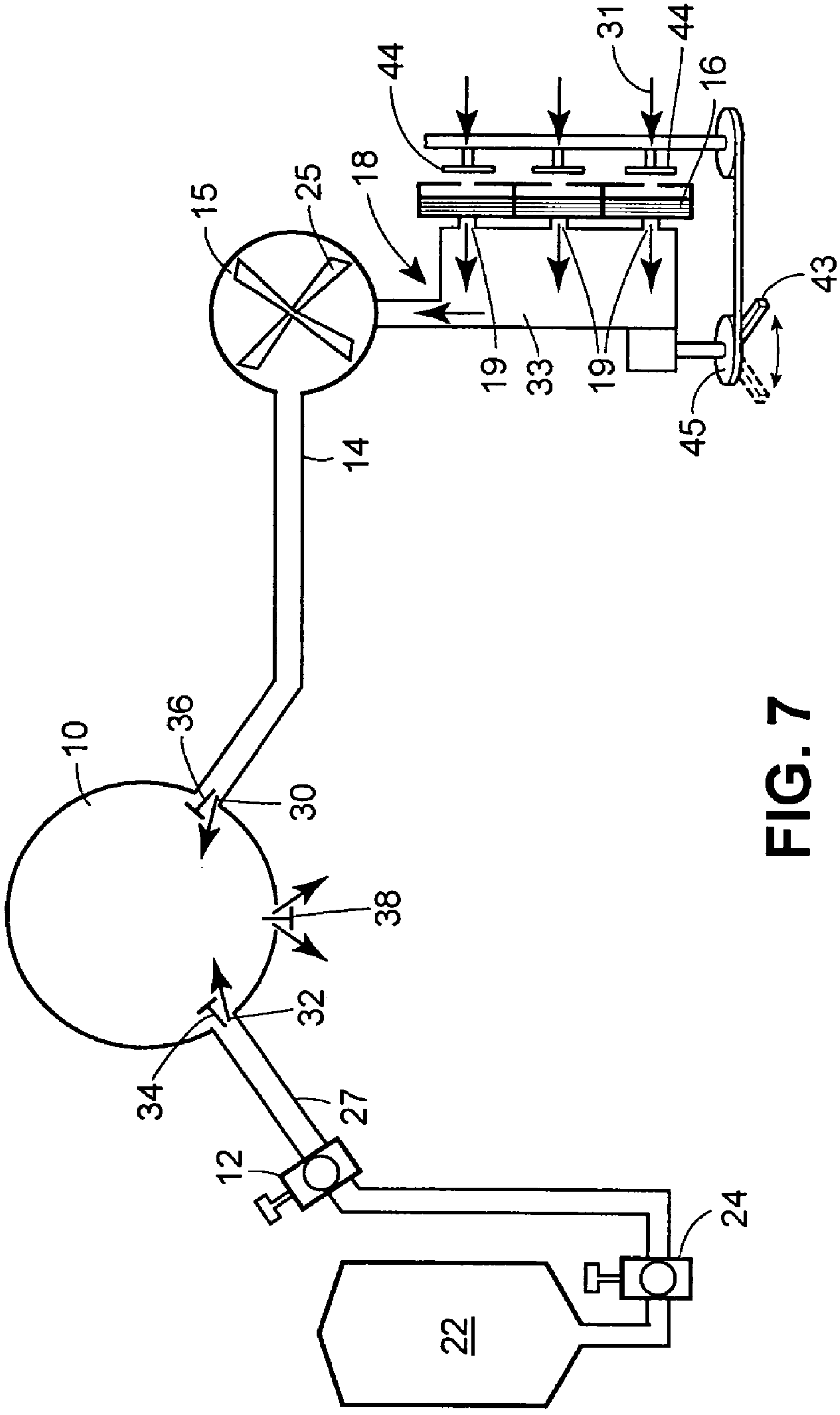

In FIGS. 3,4 and 5 the face mask 10 is shown to be connected, via a hose 14*a*, to a plenum 21 which in turn, is connected to both a compressed air bottle 22 via a hose 27. The plenum 21 is also connected, via a hose 29 through the blower impeller 25, to the plenum chamber 18, thence to filters/decontamination canisters 16 and on to an ambient air intake 31. The air bottle 22 is connected to the plenum 21 via a hose 27, a regulator 12 and a shut off valve 24. The plenum chamber 21 has suitable valve means 34 and 36 that is adapted to control the flow of air from either the air bottle 22 or the filter/decontamination canisters 16. The impeller fan 25 provides means for moving ambient air through the intake 31 and through the filter/decontamination canisters into the face mask.

The filter/canister plenum chamber 18 supports at least one, and preferably a plurality of filters or canisters 16. The exit 19 from each canister is preferably operatively associated with the mask plenum 21 so that contaminated air drawn into each filter/decontamination canister 16 by means of the motor driven fan 25 is cleaned and then powered by the fan 25 into the face mask 10 via the hose 14*a* and the regulator valving system 21.

In FIGS. 1 and 2 here are shown three (3) canisters 16 each of which contain filter medium. One or more of the canisters can also contain suitable materials that serve to decontaminate the ambient environmental air by eliminating harmful components that are not filterable.

The canisters can be assembled, in a preferred embodiment, so that each canister has a separate intake opening 20 and a separate exit 19. All air passing through any and all specific filter/decontamination canister(s) exit into a manifold plenum 18, having an air collection chamber 33, that is operatively associated with the fan means 25 as stated above. The individual filter/decontamination canisters can be used individually or in plural configuration and may be fitted all on one side of the filter plenum chamber 18 or fitted some one side and some the other to the desired quantity.

A lever handle or rotary handle 43 is connected to filter cover(s) 44 and the motor on/off switch 45. In the semi-automatic or automatic mode the lever 43 can be solenoid operated. In the motor-off position, the filter cover(s) is disposed over the air entry port(s) of the filter/decontamination canister(s) thereby preventing any air from entering the filter/decontamination canister(s). This function provides that while the apparatus is operating in a SCBA mode in a contaminated atmosphere, the filter/decontamination canisters are not taking in any contaminated air and therefore are not becoming unnecessarily contaminated. By being linked to the on/off switch, this ensures that the filter/decontamination canister(s) airways are open when the PAPR is switched on.

The air cylinder 22 is assembled into a conventional harness 17 and operatively associated with the PAPR manifold plenum chamber 21 such that air released from the air cylinder bypasses the filter media in the canisters and proceeds directly to the plenum chamber 21 and thence through the hose 14*a* into the face mask 10. A gas pressure regulator 12 is required for use with the bottled air in order to let the bottle pressure down to a pressure that is manageable by the user.

It should be noted that the plenum 21 can be operated in any of three modes. Under manual control, starting in PAPR mode, the PAPR would be on, the main cylinder 22 valve would be open, the second stage regulator 12 would be closed, the valve 34 in the plenum 21 would be closed and valve 36 would be open due to the pressure of air from the blower motor assembly 15. When the wearer determines that the atmosphere is in danger of becoming un-breathable or contaminated by a challenge greater than that the filter canisters being worn, are designed to take, the wearer will open the second stage regulator 12, the resultant air pressure will open valve 34 and air will pass into the plenum 21. The resultant pressure in the plenum 21 will close the valve 36 shutting off air from the PAPR. The wearer will now be breathing only bottled air. The wearer will switch off the power supply to the PAPR blower motor 15.

In semi-automatic or automatic mode, starting in PAPR mode, the PAPR would be on, the main cylinder 22 valve would be open, the second stage regulator 12 would be closed, the valve 34 in the plenum 21 would be closed and valve 36 would be open due to the pressure of air from the blower motor assembly 15. When by means of sensors it is determined that the atmosphere is in danger of becoming un-breathable or contaminated by a challenge greater than that the filter canisters being worn, are designed to take, the system will sound an audible alarm which instructs the wearer to open the second stage regulator 12, the resultant air pressure will open valve 34 and air will pass into the plenum 21 or, the system will automatically open valve 34, valve 36 would close and the PAPR switched off.

In fully automatic mode, starting in PAPR mode the PAPR would be on, the main cylinder 22 valve would be open, the second stage regulator 12 would be open, the valve 34 would be held closed electrically, or electro-mechanically, in the plenum 21 and valve 36 would be open due to the pressure of air from the blower motor assembly 15. When by means of sensors it is determined that the atmosphere is in danger of becoming un-breathable or contaminated by a challenge greater than that the filter canisters being worn, are designed to take, the system will switch the control to valve 34 which would then open, and air will pass into the plenum 21 closing valve 36 and then the PAPR would be switched off.

What is claimed is:

1. A breathing apparatus comprising:

a tank adapted to contain air under pressure operatively associated with a regulator to enable delivery of said pressurized air to a user of said apparatus;

a filter/canister system adapted to enable ambient air to pass through a filter medium having a mesh that is sufficient to trap solid particles in ambient air and/or to enable ambient air in need of cleaning to have a residence time in contact with media that is sufficient to decontaminate contaminating vapors and gases from said ambient air to form clean air;

means for moving said ambient air into said filter system, through said filter medium in said filter system and thence into operative relationship with a user of the apparatus during said filtered air mode;

a valve assembly comprising a first valve associated with said tank and a second valve associated with said filter system, the valve assembly adapted to control the flow of cleaned air from said filter system in said filtered mode and pressurized air from said tank in said clean air mode, a flow path defined between the tank and valve assembly, the regulator being disposed between the tank and valve assembly along the flow path and reducing air pressure of the pressurized air to resultant air pressure, such that the resultant air pressure opens said first valve and closes said second valve to actuate said valve assembly from the filtered mode to the clean air mode while continuously providing a supply of breathable air to the user;

and a first switch operably coupled to the tank and selectively enabling switching between the clean air mode and the filtered air mode.

2. An apparatus as claimed in claim 1 further comprising plural filter elements.

3. An apparatus as claimed in claim 1 further comprising a face mask adapted to tightly fit a user.

4. An apparatus as claimed in claim 3 wherein the valve assembly includes a first conduit between said tank and said face mask, a second conduit between said filter system and said face mask, and one or more valves operatively associated with said first and second conduits adapted to control the flow of cleaned air from said filter system or air from said tank to said user.

5. The breathing apparatus of claim 4, wherein the one or more valves of the valve assembly comprises a valve operatively connected to said second conduit such that said pressurized air supplied from said tank during said clean air mode engages and closes said valve.

6. The breathing apparatus of claim 4, wherein said first conduit is connected directly between said regulator and said face mask and said second conduit is connected directly between said filter system and said face mask.

7. An apparatus as claimed in claim 3, further comprising a one way exhaust valve operatively associated with said face mask.

8. The breathing apparatus of claim 1, further comprising a second switch associated with the means for moving and coupled to the valve assembly, the second switch adapted to control energization of the means for moving in conjunction with operation of the valve assembly.

9. An apparatus as claimed in claim 8, wherein the second switch is user actuatable.

10. An apparatus as claimed in claim 8, wherein the second switch is coupled to the valve assembly to energize the moving means when the valve assembly is set to control the flow of cleaned air from the filter system and to de-energize the moving means when the valve assembly is set to control pressurized air from the pressure tank.

11. The breathing apparatus of claim 10, wherein the second switch de-energizes the means for moving after the pressurized air from said tank closes the second valve such that a user is simultaneously supplied with pressurized air from said tank and ambient air from said filter system during the actuation of the valve assembly from the filtered air mode to the clean air mode.

12. The breathing apparatus of claim 1, wherein the first switch comprises a manually operable valve of the regulator.

13. The breathing apparatus of claim 1, wherein the pressurized air from said tank overcomes the ambient air from the filter system to close the second valve.

14. A breathing apparatus comprising:

a tank adapted to contain air under pressure;

a regulator coupled to the tank to enable delivery of said pressurized air to a user of the apparatus in a clean air mode;

a filter system adapted to enable ambient air to pass through a filter medium;

a powered air flow unit that forces ambient air into said filter system, and through said filter medium to deliver filtered air into operative relationship with said user of the apparatus in a filtered air mode;

a valve assembly comprising a first valve associated with said tank and a second valve associated with said filter system, a flow path defined between the tank and valve assembly, the regulator being disposed between the tank and the valve assembly along the flow path and reducing air pressure of the pressurized air to a resultant air pressure, such that the resultant air pressure opens said first valve and closes said second valve to actuate said valve assembly from the filtered mode to the clean air mode while continuously providing a supply of breathable air to the user; and a first switch operably connected to the tank and selectively enabling switching between the clean air mode and the filtered air mode.

15. The breathing apparatus of claim 14, further including a face mask adapted to tightly fit a user fluidly coupled to the valve assembly.

16. The breathing apparatus of claim 15, wherein the filter medium includes a mesh that is sufficient to trap solid particles in ambient air.

17. The breathing apparatus of claim 15, wherein the filter medium includes a media that is sufficient to decontaminate contaminating vapors and gases from ambient air.

18. The breathing apparatus of claim 15, wherein the valve assembly includes a first conduit disposed between said tank and said face mask, a second conduit disposed between said filter assembly and said face mask, and one or more valves operatively associated with said first and second conduits to control the flow of cleaned air from said filter assembly or air from said tank to said face mask.

19. The breathing apparatus of claim 18, wherein the one or more valves of the valve assembly comprises a valve operatively connected to said second conduit such that said pressurized air supplied from said tank during said clean air mode engages and closes said valve.

20. The breathing apparatus of claim 18, wherein said first conduit is connected directly between said regulator and said face mask and said second conduit is connected directly between said filter assembly and said face mask.

21. The breathing apparatus of claim 15, wherein the filter medium includes plural filter elements.

22. The breathing apparatus of claim 15, further comprising a one way exhaust valve operatively associated with said face mask.

23. The breathing apparatus of claim 14, further comprising a second switch associated with the powered air flow unit, the second switch adapted to control energization of the powered air flow unit in conjunction with the operation of the valve assembly.

24. The breathing apparatus of claim 23, wherein the second switch is coupled to the valve assembly to energize the powered air flow unit when the valve assembly controls the flow of cleaned air from the filter system and to de-energize the powered air flow unit when the valve assembly controls pressurized air from the pressure tank.

25. The breathing apparatus of claim 24, wherein the second switch de-energizes the powered air flow unit after the pressurized air from said tank closes the second valve such that a user is simultaneously supplied with pressurized air from said tank and ambient air from said filter system during the actuation of the valve assembly from the filtered air mode to the clean air mode.

26. The breathing apparatus of claim 14, wherein the first switch comprises a manually operable valve of the regulator.

27. The breathing apparatus of claim 14, wherein the pressurized air from said tank overcomes the ambient air from the filter system to close the second valve.

28. A breathing apparatus comprising:

a tank adapted to contain air under pressure operatively associated with a regulator to enable delivery of said pressurized air to a user of said apparatus during a clean air mode;

a filter system adapted to enable ambient air to pass through a filter medium to deliver filtered air to said user of said apparatus during a filtered air mode, the filter medium having a mesh that is sufficient to trap solid particles in ambient air and enable ambient air in need of cleaning to have a residence time in contact with media that is sufficient to decontaminate contaminating vapors and gases from said ambient air to form clean air;

means for moving said ambient air into said filter system, through said filter medium in said filter system and thence into operative relationship with a user of the apparatus during said filtered air mode;

a valve assembly comprising a first valve associated with said tank and a second valve associated with said filter system, the valve assembly adapted to control the flow of cleaned air from said filter system in said filtered mode and pressurized air from said tank in said clean air mode; and a flow path defined between the tank and valve assembly, the regulator being disposed between the tank and valve assembly along the flow path and reducing air pressure of the pressurized air to a resultant air pressure, such that the resultant air pressure opens said first valve and closes said second valve to actuate said valve assembly from the filtered mode to the clean air mode while continuously providing a supply of breathable air to the user.

* * * * *

UNITED STATES PATENT AND TRADEMARK OFFICE

CERTIFICATE OF CORRECTION

PATENT NO. : 7,543,584 B2
APPLICATION NO. : 10/675135
DATED : June 9, 2009

INVENTOR(S) : Michael J. Brookman

It is certified that error appears in the above-identified patent and that said Letters Patent is hereby corrected as shown below:

At Column 7, line 21, “apparatus;” should be -- apparatus during a clean air mode; --.

At Column 7, line 22, “filter/canister” should be -- filter --.

At Column 7, line 23, “medium having” should be -- medium to deliver filtered air to said user of said apparatus during a filtered air mode, the filter medium having --.

At Column 7, line 24, “and/or to” should be -- and --.

At Column 8, line 17, “moving means” should be -- means for moving --.

Signed and Sealed this

Sixteenth Day of February, 2010

David J. Kappos

David J. Kappos
*Director of the United States Patent and Trademark Office*